(12) United States Patent
Cave

(10) Patent No.: US 10,159,795 B2
(45) Date of Patent: Dec. 25, 2018

(54) DRUG DELIVERY DEVICE

(71) Applicant: SANOFI-AVENTIS DEUTSCHLAND GMBH, Frankfurt am Main (DE)

(72) Inventor: George Cave, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 541 days.

(21) Appl. No.: 14/763,868

(22) PCT Filed: Jan. 27, 2014

(86) PCT No.: PCT/EP2014/051473
§ 371 (c)(1),
(2) Date: Jul. 28, 2015

(87) PCT Pub. No.: WO2014/118110
PCT Pub. Date: Aug. 7, 2014

(65) Prior Publication Data
US 2015/0367075 A1 Dec. 24, 2015

(30) Foreign Application Priority Data
Jan. 29, 2013 (EP) ..................... 13153140

(51) Int. Cl.
*A61M 5/31* (2006.01)
*A61M 5/20* (2006.01)
(Continued)

(52) U.S. Cl.
CPC ............ *A61M 5/3134* (2013.01); *A61M 5/20* (2013.01); *A61M 5/34* (2013.01); *A61M 5/345* (2013.01);
(Continued)

(58) Field of Classification Search
CPC .. A61M 5/31571; A61M 5/3134; A61M 5/20; A61M 5/24; A61M 2005/3117;
(Continued)

(56) References Cited

U.S. PATENT DOCUMENTS 5,401,251 A * 3/1995 Hui ..................... A61M 5/3216
604/192
6,171,276 B1 * 1/2001 Lippe ..................... A61M 5/20
128/DIG. 1

(Continued)

FOREIGN PATENT DOCUMENTS

| WO | 2008/045203 | 4/2008 |
|---|---|---|
| WO | 2009/113060 | 9/2009 |
| WO | 2011/117404 | 9/2011 |

OTHER PUBLICATIONS

European Search Report for EP App. No. 13153140.2, dated May 6, 2013.
(Continued)

*Primary Examiner* — Jenna Zhang
(74) *Attorney, Agent, or Firm* — Fish & Richardson P.C.

(57) ABSTRACT

A drug delivery device for administering a drug is presented having a body adapted to retain a cartridge containing a drug, at least one electrical unit and a port for electrically contacting the electrical unit, an adapter for attaching an injection needle to the drug delivery device, a safety mechanism arranged to prevent access to the port while an injection needle is in fluid communication with the cartridge and arranged to prevent establishing a fluid communication between an injection needle and the cartridge while the port is accessible.

14 Claims, 6 Drawing Sheets

(51) Int. Cl.
*A61M 5/34* (2006.01)
*A61M 5/24* (2006.01)

(52) U.S. Cl.
CPC ............. *A61M 5/347* (2013.01); *A61M 5/24* (2013.01); *A61M 2005/206* (2013.01); *A61M 2205/50* (2013.01); *A61M 2205/502* (2013.01); *A61M 2205/8237* (2013.01); *A61M 2205/8262* (2013.01)

(58) Field of Classification Search
CPC .......... A61M 2005/2073; A61M 5/347; A61M 5/345; A61M 2005/206; A61M 2205/8237; A61M 2205/50; A61M 2205/502; A61M 2205/8262
See application file for complete search history.

(56) References Cited

U.S. PATENT DOCUMENTS

| | | | |
|---|---|---|---|
| 7,648,483 B2* | 1/2010 | Edwards | A61M 5/19 604/140 |
| 7,704,231 B2* | 4/2010 | Pongpairochana | A61M 5/20 604/134 |
| 8,206,351 B2* | 6/2012 | Sugimoto | A61M 5/20 604/151 |
| 9,155,837 B2* | 10/2015 | Kemp | A61M 5/2033 |
| 9,339,605 B2* | 5/2016 | Wimpenny | A61M 5/002 |
| 2005/0090781 A1* | 4/2005 | Baba | G06F 19/00 604/209 |
| 2005/0228346 A1 | 10/2005 | Goode et al. | |
| 2007/0197968 A1* | 8/2007 | Pongpairochana | A61M 5/20 604/131 |
| 2010/0087799 A1* | 4/2010 | Galbraith | A61M 5/2448 604/518 |
| 2011/0201999 A1* | 8/2011 | Cronenberg | A61M 5/2066 604/89 |
| 2012/0130346 A1* | 5/2012 | Davies | A61M 5/2448 604/506 |
| 2013/0079708 A1* | 3/2013 | Wimpenny | A61M 5/24 604/65 |
| 2013/0245604 A1* | 9/2013 | Kouyoumjian | A61M 5/1408 604/506 |
| 2013/0310756 A1* | 11/2013 | Whalley | G06F 19/00 604/189 |
| 2014/0142507 A1* | 5/2014 | Armes | A61M 5/422 604/112 |
| 2014/0194830 A1* | 7/2014 | Nzike | A61M 5/31541 604/211 |
| 2015/0182706 A1* | 7/2015 | Wurmbauer | A61M 5/34 604/111 |
| 2015/0320932 A1* | 11/2015 | Draper | A61M 5/20 604/131 |
| 2015/0359967 A1* | 12/2015 | Steel | A61M 5/20 604/241 |
| 2015/0367074 A1* | 12/2015 | Draper | A61M 5/20 604/198 |
| 2016/0296700 A1* | 10/2016 | Kikuchi | A61M 5/36 |

OTHER PUBLICATIONS

International Search Report and Written Opinion for Int. App. No. PCT/EP2014/051473, dated Mar. 7, 2014.

* cited by examiner

DRUG DELIVERY DEVICE

CROSS REFERENCE TO RELATED APPLICATIONS

The present application is a U.S. National Phase Application pursuant to 35 U.S.C. § 371 of International Application No. PCT/EP2014/051473 filed Jan. 27, 2014, which claims priority to European Patent Application No. 13153140.2 filed Jan. 29, 2013. The entire disclosure contents of these applications are herewith incorporated by reference into the present application.

TECHNICAL FIELD

The invention relates to a drug delivery device.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring. In other devices this is achieved by an electromechanical drive. Devices with electromechanical and/or electronic components may comprise a port which may serve for wired communication with another device for data transfer or for charging.

SUMMARY

It is an object of the present invention to provide an improved drug delivery device.

The object is achieved by a drug delivery device according to claim 1.

Preferred embodiments of the invention are given in the dependent claims.

According to the invention a drug delivery device for administering a drug comprises:
  a body adapted to retain a cartridge containing a drug,
  at least one electrical unit and a port for electrically contacting the electrical unit,
  an adapter for attaching an injection needle to the drug delivery device,
  a safety mechanism arranged to prevent access to the port whilst an injection needle is in fluid communication with the cartridge and arranged to prevent establishing a fluid communication between an injection needle and the cartridge whilst the port is accessible.

The port, e.g. a USB port, may serve for wired communication with another device for data transfer or charging. The safety mechanism avoids the risk that the user may inadvertently leave the drug delivery device connected via a cable whilst attempting to inject. In this case there may exist a potential conductive path from the externally connected device, through the cable, the port and the electronics of the drug delivery device to the patient via the conductive metal injection needle. In case of a current overload on the port or a leaking cartridge which creates a short-circuit within the drug delivery device, the patient would be subjected to an electric shock. An electric shock may occur either if both the patient and the external device connected to the port are grounded or if the patient touches the port whilst they were injecting regardless of whether a cable is connected to the port or not. Similarly, the port may be adapted to interface with a blood glucose strip for measuring a user's blood glucose value. The port will thus also feature electronic contacts. Consequently there is a similar associated risk. The safety mechanism according to the invention prevents this risk.

The above risk is addressed by providing a safety mechanism arranged to prevent access to the port whilst an injection needle is in fluid communication with the cartridge and arranged to prevent establishing a fluid communication between an injection needle and the cartridge whilst the port is accessible.

Other options would be to have the safety mechanism disable the dosing operation of the drug delivery device when the user can access the port. This may be achieved by performing an operation which disables a delivery mechanism of the drug delivery device or by preventing the user from accessing a button or soft button on a human-machine interface for operating the drug delivery device.

In an exemplary embodiment the body comprises a main part and a movable body component movable relative to the main part between an aligned position, in which the port is accessible and a misaligned position in which the port is covered, wherein the adapter is arranged on the body such that the adapter is split when the movable body component is in the misaligned position preventing attachment of a needle, wherein the adapter is arranged to prevent movement of the movable body component from the aligned position into the misaligned position when a needle is attached.

In the aligned position the port may be hidden by the movable body component or by a sliding door coupled to the movable body component.

A link mechanism providing a displacement gain may be arranged for coupling the sliding door to the movable body component thus allowing a relatively small movement of the movable body component or caused by the movable body component to cause a greater movement of the sliding door.

In an exemplary embodiment a retaining pin coupled to the sliding door and biased towards the movable body component is arranged to be engaged by the movable body component in the aligned position and disengaged in the misaligned position thus providing a simple means for translating the sliding door in one direction while moving the movable body component in another direction or sense.

In an exemplary embodiment the movable body component is arranged to translate and/or rotate between the aligned position and the misaligned position.

In another exemplary embodiment the movable body component may be detachable from the main part in the misaligned position.

In an exemplary embodiment the movable body component encompasses substantially a quarter sector of the adapter, e.g with the cross section of a quarter circle. This enables the diameter of the adapter to be kept small enough to accept a type A needle whilst still ensuring that the action of splitting the adapter by rotating the movable body component prevents the needle from being fitted to the adapter and does not cause an interference around the threaded area between the movable body component and the cartridge.

In an exemplary embodiment an inner surface of the movable body component is formed to define two edges, one of them radially supporting the cartridge when the movable body component is in the aligned position and the other one radially supporting the cartridge when the movable body component is in the misaligned position. This ensures that the cartridge remains restrained within the body regardless of the position of the movable body component.

In an exemplary embodiment the edges are defined by a number if circumferential ribs formed within the movable body component. The ribs may be moulded in the movable body component. A profile of the ribs may be designed to curve smoothly between the aligned and the misaligned position and thus avoid any interference between the movable body component and the cartridge.

In an exemplary embodiment the adapter comprises a threaded area for engaging a threaded needle hub of a needle. Instead of the threaded area the adapter may comprise other means for attaching the needle such as a bayonet fit, a cone or a Luer-lock.

In an exemplary embodiment the translation of the movable body component between the aligned position and the misaligned position may comprise an axial component and/or a radial component. For instance, the movable body component could slide both out and up, to lift away from the main part of the body at an angle.

In an exemplary embodiment the movable body component is arranged to rotate about pivot point or hinge defining a pivot axis having a longitudinal and/or transversal direction component. For example the movable body component may rotate about a transversal or longitudinal axis or any other axis. Likewise the rotational axis of the movable body component may be inclined in any other direction.

In an exemplary embodiment a spring is arranged for biasing the movable body component towards the aligned position or towards the misaligned position.

In an exemplary embodiment a restraint mechanism is arranged for limiting movement of the movable body component, in particular towards the misaligned position.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
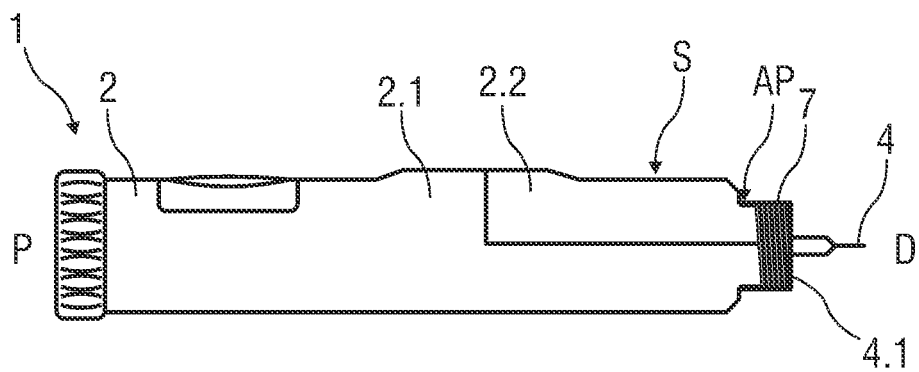
FIG. 1 is a schematic view of a first exemplary embodiment of an electromechanical drug delivery device for administering a drug, comprising a body with a movable body component in an aligned position, wherein an injection needle is mounted to an adapter on the body.
Figure 2:
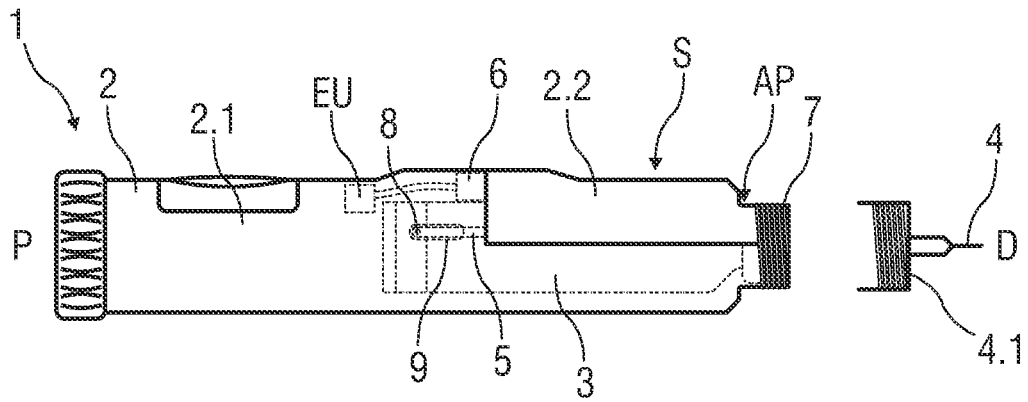
FIG. 2 is a schematic view of the first exemplary embodiment of the electromechanical drug delivery device with the injection needle removed.
Figure 3:
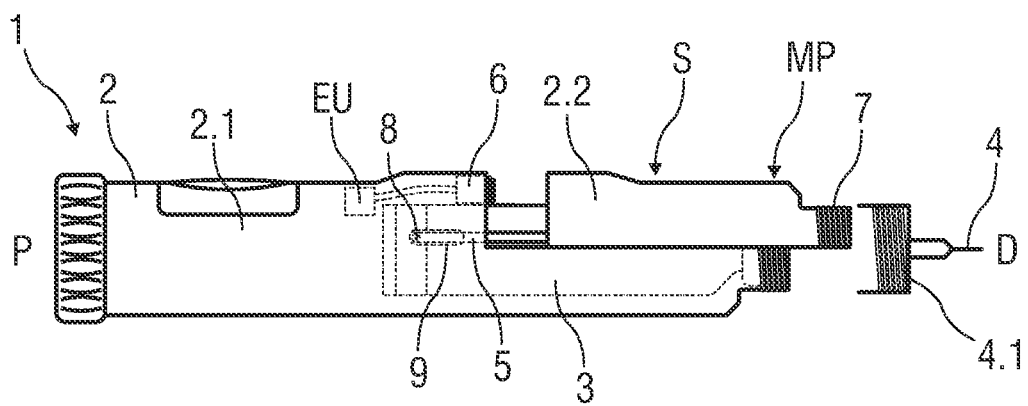
FIG. 3 is a schematic view of the first exemplary embodiment of the electromechanical drug delivery device with the movable body component in a misaligned position.

FIGS. 1 to 3 are schematic views of a first exemplary embodiment of an electromechanical drug delivery device 1 for administering a drug. The drug delivery device 1 comprises a body 2 with a main part 2.1 adapted to receive a drug cartridge 3 or syringe. A hypodermic needle 4 may be attached to the cartridge 3, preferably a needle 4 with two tips, one of them for piercing an injection site and the other for piercing a septum on the cartridge 3 for establishing a fluid communication between the cartridge 3 and the needle 4. The drug delivery device 1 further comprises at least one electrical unit (EU) such as a control unit and/or a human-machine-interface for communicating information to a user and for allowing the user to operate the drug delivery device and/or an electromechanical drive (not illustrated) for inserting the needle 4 into an injection site, e.g. a patient's skin and/or dispensing drug from the cartridge 3 through the needle 4 and/or retracting the needle 4 post-injection.

The body 2 comprises an adapter 7 for attaching the needle 4. The adapter 7 may be arranged as a threaded area 7. The needle 4 may be attached and removed by the user thus allowing it to be used for a single delivery of the drug. After delivery the needle 4 is removed, discarded and replaced by a new one, if applicable.

The drug delivery device 1 comprises a port 6 which may serve for wired communication with another device for data transfer or charging. There is an associated risk with this feature that the user may inadvertently leave the drug delivery device 1 connected via a cable whilst attempting to inject. Whilst a control unit of the drug delivery device 1 may run software including checks to prevent the delivery of the drug in this situation, there will still exist a potential conductive path from the externally connected device, through the cable, the port 6 and the electronics of the drug delivery device 1 to the patient via the conductive metal needle 4. It is thus possible that, for instance, a current overload on the port 6 or a leaking cartridge 3 which creates a short-circuit within the drug delivery device 1, could deliver an electric shock to the patient. This may occur either if both the patient and the external device connected to the port 6 are grounded or if the patient touches the port 6 whilst they were injecting regardless of whether a cable is connected to the port 6 or not.

Similarly, the port 6 may be adapted to interface with a blood glucose strip for measuring a user's blood glucose value. The port 6 will thus also feature electronic contacts. Consequently there is a similar associated risk.

The above risk is addressed by providing a safety mechanism S to disable the dosing operation of the drug delivery device 1 when the user can access the port 6. This is achieved by performing an operation which disables a delivery mechanism of the drug delivery device 1 or by preventing the user from accessing the adapter 7 of the drug delivery device 1 adapted to connect to the needle 4 or from accessing a button or soft button on a human-machine interface.

In the embodiment of FIG. 1 the body 2 comprises a movable body component 2.2 towards a distal end of the body 2. The adapter 7, in particular the threaded area 7 is arranged in part on the movable body component 2.2 and in part on the main part 2.1 of the body 2. The movable body component 2.2 can be moved axially relative to the main part 2.1 between a proximal aligned position AP as in FIGS. 1 and 2, axially aligned with the main part 2.1 of the body 2 such that the threaded area 7 allows for attaching a needle 4, and a distal misaligned position MP as in FIG. 3, where the movable body component 2.2 is axially misaligned with the main part 2.1 of the body 2 thus preventing attachment of a needle 4. If a needle 4 is attached to the adapter 7 the movable body component 2.2 is prevented from being moved out of the aligned position AP as the threads of the adapter 7 and of a needle hub 4.1 are engaged. The port 6 is arranged within the main part 2.1 and can only be accessed when the movable body component 2.2 is in its misaligned position MP.

A slide restraint 5 is arranged on the movable body component 2.2 and comprises a pin 8 engaged in a restraining slot 9 arranged in the main part 2.1 to ensure that the motion of the movable body component 2.2 is constrained to a single axis and a limited range. Likewise the slide restraint 5 could be arranged on the main part 2.1 and the restraining slot 9 in the movable body component 2.2.

In FIG. 1 a needle 4 is attached to the adapter 7 thus preventing the movable body component 2.2 from being moved out of the aligned position AP. In order to access the port 6 the user unscrews the needle 4 from the adapter 7 as in FIG. 2 thus allowing separation of the main part 2.1 and the movable body component 2.2. The movable body component 2.2 is then moved into the misaligned position MP splitting the thread on the adapter 7 and exposing the port 6. Due to the split adapter 7 a needle 4 cannot be attached while the port 6 is accessible.

In an exemplary embodiment at least one spring may be arranged to bias the movable body component 2.2 either towards the misaligned position MP or towards the aligned position AP.

In another exemplary embodiment the movable body component 2.2 may be connected to the main part 2.1 such that it moves in a different plane of motion. For instance, the movable body component 2.2 could slide both out and up, to lift away from the main part 2.1 of the body 2 at an angle. Likewise the movable body component 2.2 may be arranged to detach completely from the main body 2.1 as an entirely separate component. Any link mechanism allowing splitting the threaded area of the adapter 7 may be suitable.

Figure 4:
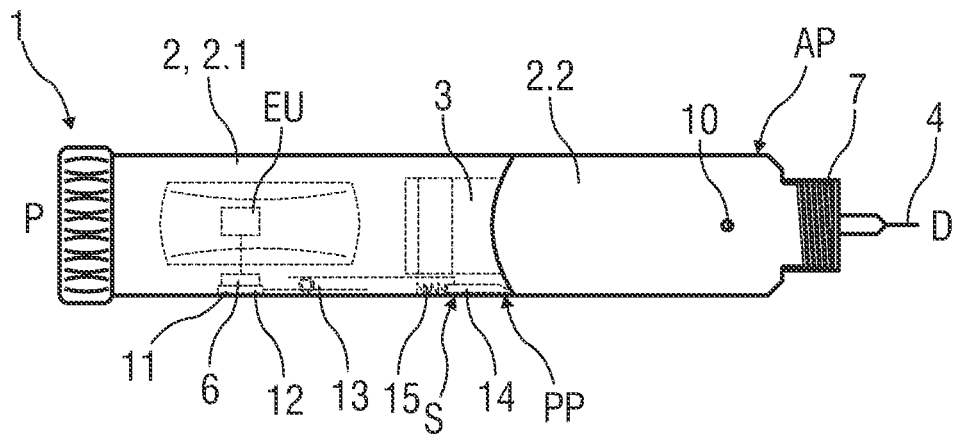
FIG. 4 is a side view of a second exemplary embodiment of the drug delivery device comprising a body with a movable body component in an aligned position, wherein an injection needle is mounted to an adapter on the body.

FIG. 4 is a side view of another exemplary embodiment of the drug delivery device 1.

The drug delivery device 1 comprises a body 2 with a main part 2.1 adapted to receive a drug cartridge 3 or syringe. A hypodermic needle 4 may be attached to the cartridge 3. The drug delivery device 1 further comprises at least one electrical unit such as a control unit and/or a human-machine-interface for communicating information to a user and for allowing the user to operate the drug delivery device and/or an electromechanical drive (not illustrated) for inserting the needle 4 into an injection site, e.g. a patient's skin and/or dispensing drug from the cartridge 3 through the needle 4 and/or retracting the needle 4 post-injection.

The body 2 comprises an adapter 7 for attaching the needle 4. The adapter 7 may be arranged as a threaded area 7. The needle 4 may be attached and removed by the user thus allowing it to be used for a single delivery of the drug. After delivery the needle 4 is removed, discarded and replaced by a new one, if applicable.

The drug delivery device 1 comprises a port 6 which may serve for wired communication with another device for data transfer or charging.

In the embodiment of FIG. 4 the body 2 comprises a movable body component 2.2 towards a distal end of the body 2. The adapter 7, in particular the threaded area 7 is arranged in part on the movable body component 2.2 and in part on the main part 2.1 of the body 2. The movable body component 2.2 is rotatably arranged about a pivot point 10 defining a substantially transversal axis relative to longitudinal axis of the drug delivery device 1. The movable body component 2.2 can be rotated relative to the main part 2.1 between an aligned position AP as in FIG. 4, flush with the main part 2.1 of the body 2 such that the threaded area of the adapter 7 allows for attaching a needle 4, and a misaligned position MP as in FIG. 5, where the movable body component 2.2 is rotationally misaligned with the main part 2.1 of the body 2 thus splitting the adapter 7 and preventing attachment of a needle 4. If a needle 4 is attached to the adapter 7 the movable body component 2.2 is prevented from being moved out of the aligned position AP as the threads of the adapter 7 and of the needle hub 4.1 are engaged. The port 6 is arranged within the main part 2.1 accessible through an opening 11 in the main part 2.1. A sliding door 12 is arranged to cover or expose the opening 11. The sliding door 12 is coupled through a link mechanism 13 to a retaining pin 14 which is biased in the distal direction D by a spring 15. The link mechanism 13 causes the sliding door 12 to cover the opening 11 if the retaining pin 14 is in a proximal position PP and to expose the opening 11 if the retaining pin 14 is in a distal position DP. As in FIG. 4 the movable body component 2.2 is in the aligned position AP it engages the retaining pin 14 thus maintaining the retaining pin in the proximal position PP and preventing access to the port 6. If the movable body component 2.2 is rotated into the misaligned position MP it disengages the retaining pin 14. The retaining pin 14 is hence moved into the distal position DP by the spring 15 thus moving the sliding door 12 for exposing the opening 11 and allowing access to the port 6.

In FIG. 4 a needle 4 is attached to the adapter 7 thus preventing the movable body component 2.2 from being moved out of the aligned position AP, maintaining the retaining pin in the proximal position PP and preventing access to the port 6. In order to access the port 6 the user unscrews the needle 4 from the adapter 7 thus allowing separation of the main part 2.1 and the movable body component 2.2. The movable body component 2.2 is then rotated into the misaligned position MP splitting the thread on the adapter 7, releasing the retaining pin 14 and exposing the port 6. Due to the split adapter 7 a needle 4 cannot be attached while the port 6 is accessible.

As the movable body component 2.2 is returned to its aligned position AP by the user, the movable body component 2.2 pushes the retaining pin 14 into the proximal position PP closing the sliding door 12 to prevent access to the port 6. Engagement of the movable body component 2.2 to the retaining pin 14 may be facilitated by ramped engagement surfaces.

The link mechanism 13 may be arranged to provide a displacement gain, such that the retaining pin 14 moves half of the distance of the sliding door 12. This ensures that the retaining pin 14 can still be returned to its proximal position PP by rotation of the movable body component 2.2 into the aligned position AP. Depending upon the distance the sliding door 12 is required to move, the embodiment could be modified to remove the need for the link mechanism 13 and have the retaining pin 14 directly connect to, and actuate the motion of, the sliding door 12.

Typically, drug delivery devices 1 have a body component which fits tightly around the distal end of the cartridge 3 in order to accept a type A needle 4 and properly restrain the cartridge 3. In order to avoid interference between the threaded area 7 of the movable body component 2.2 and the distal end of the cartridge 3, in particular if a type A needle 4 and standard 3 ml cartridge 3 were used, the embodiment of FIGS. 4 and 5 may be modified as shown in FIGS. 6, 7 and 8.

Figure 6:
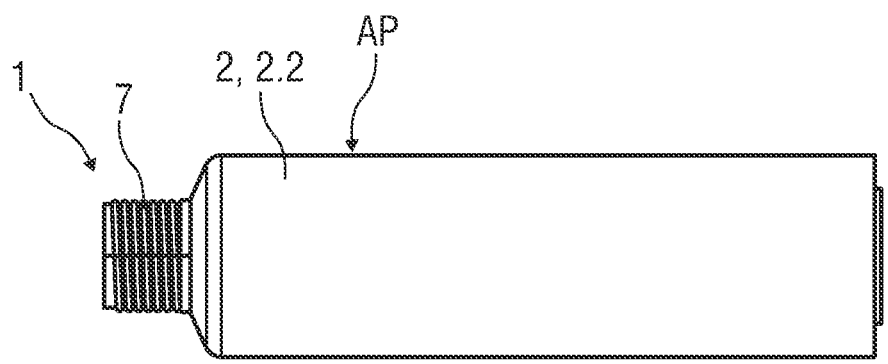
FIG. 6 is a side view of a third exemplary embodiment of the drug delivery device comprising a body with a movable body component in an aligned position.
Figure 7:
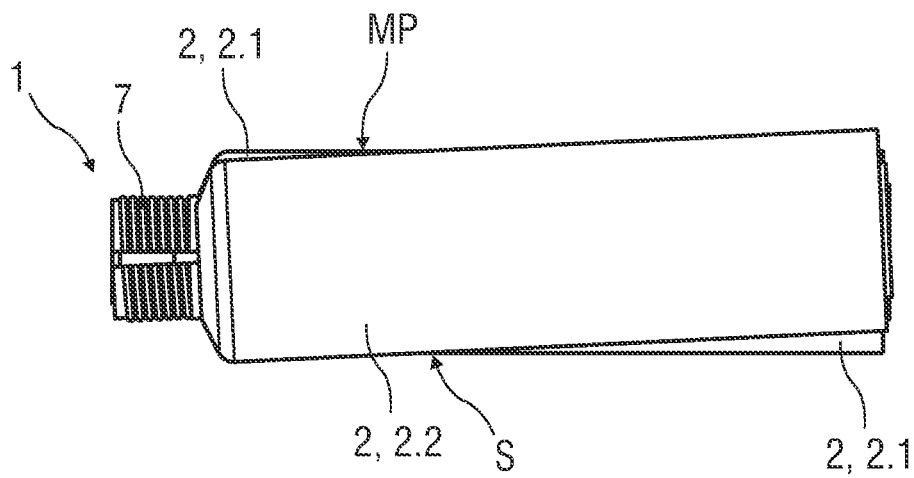
FIG. 7 is a side view of the third embodiment of the drug delivery device with the movable body component rotated into a misaligned position.
Figure 8:
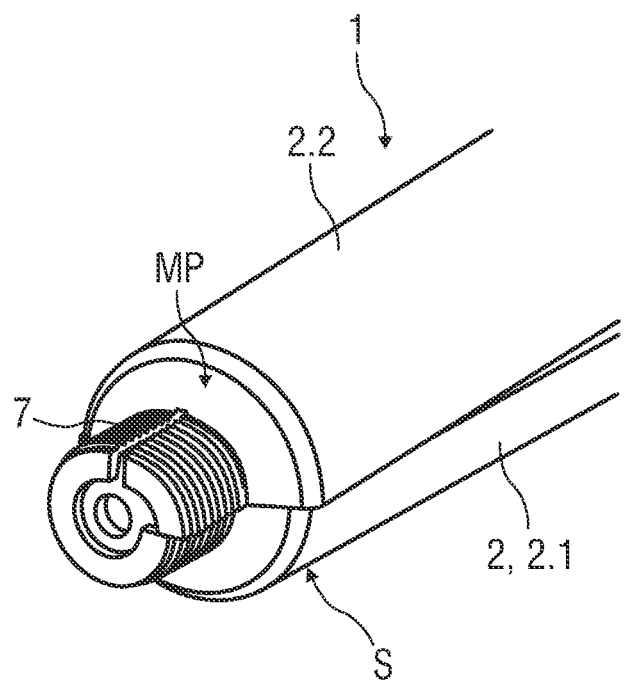
FIG. 8 is a perspective view of the third embodiment of the drug delivery device with the movable body component rotated into the misaligned position.

FIG. 6 is a schematic side view of an exemplary embodiment of the drug delivery device 1 in which the threaded area on the adapter 7 splits in a 1:3 ratio, such that the threaded area on the movable body component 2.2 encompasses substantially a quarter sector of the adapter 7 with the cross section of a quarter circle (cf. FIG. 8). This enables the diameter of the threaded area of the adapter 7 to be kept small enough to accept a type A needle 4 whilst still ensuring that the action of splitting the body 2 by rotating the movable body component 2.2 prevents the needle from being fitted to the adapter 7 and does not cause an interference around the threaded area between the movable body component 2.2 and the cartridge 3.

FIG. 6 shows the drug delivery device 1 with the movable body component 2.2 in the aligned position AP. FIG. 7 is a lateral view of the drug delivery device 1 with the movable body component 2.2 rotated into the misaligned position MP such that the threaded area of the adapter 7 is split. FIG. 8 is a corresponding perspective view.

Figure 9:
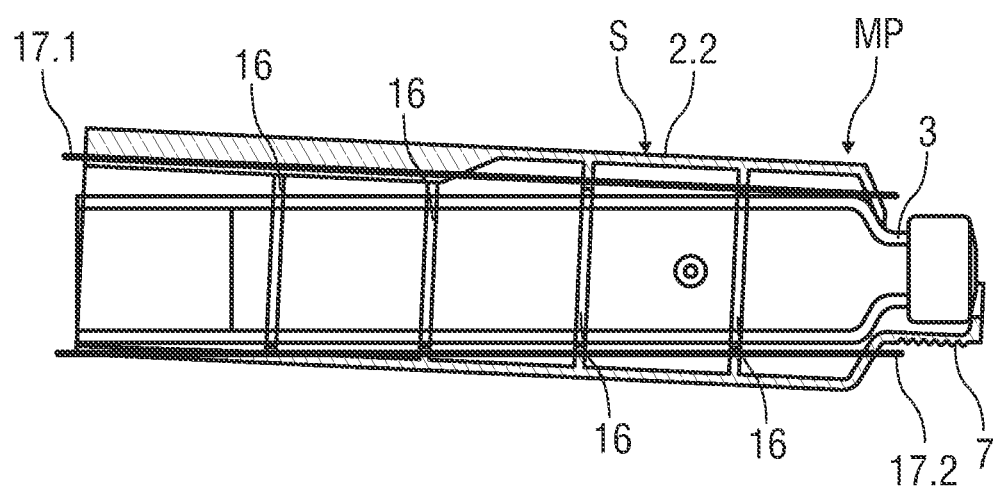
FIG. 9 is a longitudinal section of a cartridge with the movable body component in the misaligned position.

FIG. 9 is a longitudinal section of the cartridge 3 with the movable body component 2.2 in the misaligned position MP. The rotation of the movable body component 2.2 creates a misalignment with respect to the cartridge 3 which is restrained within the body 2 by the movable body component 2.2.

In order to ensure that the cartridge 3 remains restrained regardless of the position of the movable body component 2.2 a number of circumferential ribs 16 moulded in the movable body component 2.2 defines two edges 17.1, 17.2, one of them contacting the cartridge 3 when the movable body component 2.2 is in the aligned position AP and the other one contacting the cartridge 3 when the movable body component 2.2 is in the misaligned position MP.

Figure 5:
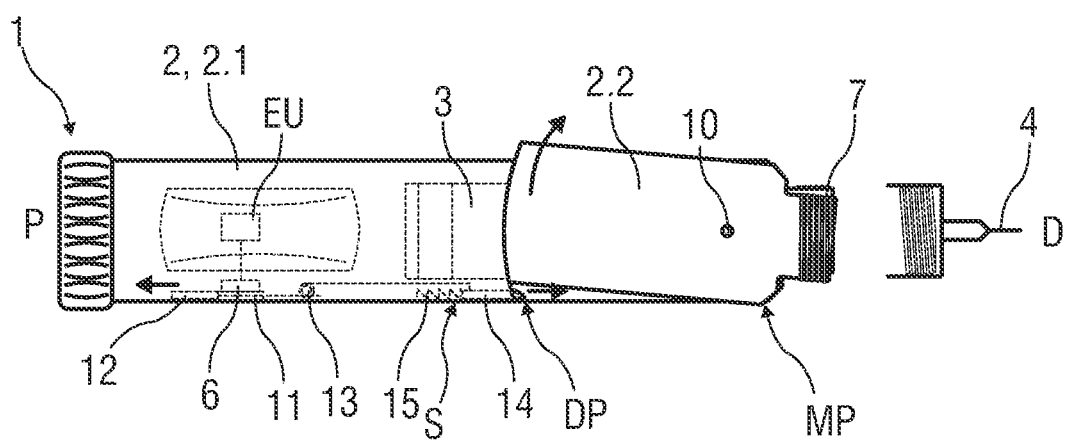
FIG. 5 is a side view of the second embodiment of the drug delivery device after removal of the injection needle and with the movable body component rotated into a misaligned position.
Figure 10:
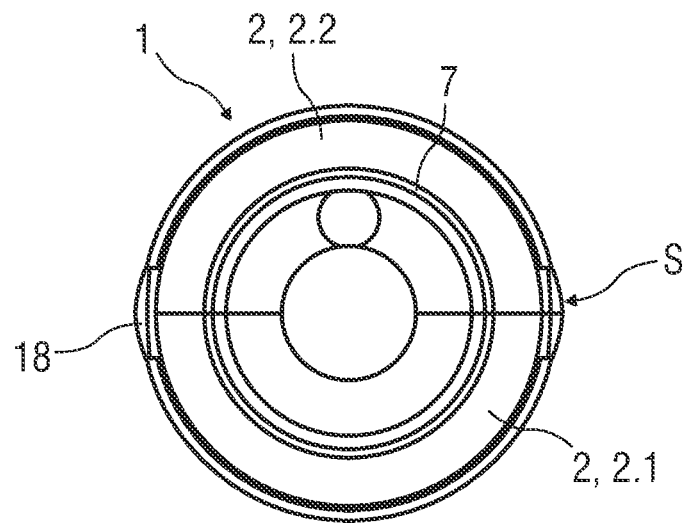
FIG. 10 is a cross sectional view of a fourth embodiment of the drug delivery device with the movable body component in the aligned position.

FIG. 10 is a cross sectional view of an embodiment of the drug delivery device 1 which is a modification of the embodiment of FIGS. 4 and 5.

Figure 11:
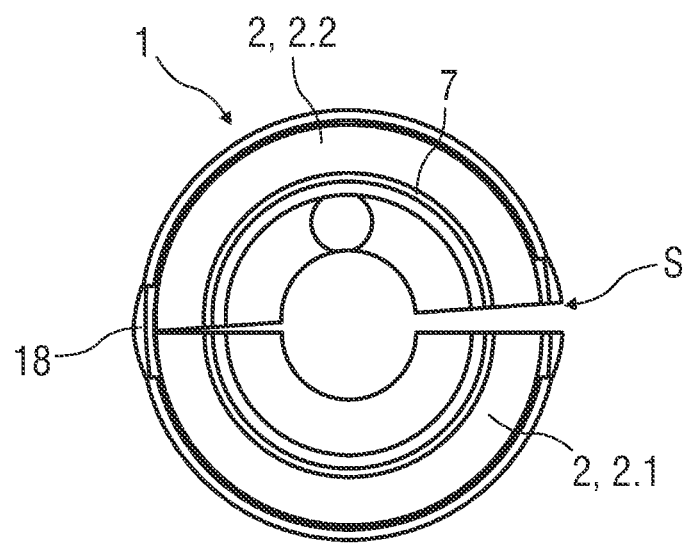
FIG. 11 is a cross sectional view of the fourth embodiment of the drug delivery device with the movable body component in the misaligned position.

Other than in the embodiment of FIGS. 4 and 5 where the movable body component 2.2 is rotated about a pivot point 10, the body 2 of the drug delivery device 1 of FIG. 10 is split axially along its side. A hinge 18 is arranged between the main part 2.1 and the movable body component 2.2 allowing the movable body component 2.2 to pivot about a longitudinal axis relative to the main part 2.1 of the body 2, so as to allow for splitting the threaded area of the adapter 7 (FIG. 11) and releasing the retaining pin (not shown in FIGS. 10 and 11) in the same manner as shown in FIGS. 4 and 5. Hinging the movable body component 2.2 about a longitudinal axis avoids interference between the cartridge 3 and the movable body component 2.2.

The safety mechanism S may in general comprise either purely mechanical means or an electronically actuated mechanical system. The safety mechanism could potentially make use of physical detents or magnetic elements to assist in the latching of the parts into the aligned or misaligned positions.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A drug delivery device for administering a drug, comprising:
   a body adapted to retain a cartridge containing a drug;
   an electrical unit;
   a port for electrically contacting the electrical unit;
   an adapter for attaching an injection needle to the drug delivery device, wherein the adaptor has a first part and a second part; and
   a safety mechanism arranged to prevent access to the port whilst the injection needle is in fluid communication with the cartridge and arranged to prevent establishing a fluid communication between the injection needle and the cartridge whilst the port is accessible,
   wherein the body comprises a main component comprising the first part of the adaptor and a movable body component comprising the second part of the adapter, wherein the movable body component is movable relative to the main component between a misaligned position, in which the port is accessible and an aligned position in which the port is covered, wherein when the movable body component is in the misaligned position, the first part and the second part are not aligned and the injection needle is prevented from attachment of the injection needle to the adapter, wherein movement of the movable body component from the aligned position into the misaligned position is prevented when the first part and the second part are aligned and the injection needle is attached to the adapter.

2. The drug delivery device according to claim 1, wherein in the aligned position, the port is hidden by the movable body component or by a sliding door coupled to the movable body component.

3. The drug delivery device according to claim 2, wherein the sliding door is coupled to the movable body component through a linkage.

4. The drug delivery device according to claim 2, wherein a retaining pin coupled to the sliding door and biased towards the movable body component is arranged to be engaged by the movable body component in the aligned position and disengaged in the misaligned position.

5. The drug delivery device according to claim 1, wherein the movable body component is arranged to translate and/or rotate between the aligned position and the misaligned position.

6. The drug delivery device according to claim 5, wherein the translation of the movable body component comprises an axial component and/or a radial component.

7. The drug delivery device according to claim 5, wherein the movable body component is arranged to rotate about a pivot point or a hinge defining a pivot axis having a longitudinal and/or a transversal direction component.

8. The drug delivery device according to claim 1, wherein the movable body component is detachable from the main component in the misaligned position.

9. The drug delivery device according to claim 1, wherein the movable body component encompasses the second part of the adapter, wherein the second part of the adapter is substantially a quarter sector of the adapter.

10. The drug delivery device according to claim 1, wherein an inner surface of the movable body component is formed to define two edges, one of the two edges radially supports the cartridge when the movable body component is in the aligned position and the other of the two edges radially supports the cartridge when the movable body component is in the misaligned position.

11. The drug delivery device according to claim 10, wherein the two edges are defined by a number of circumferential ribs formed within the movable body component.

12. The drug delivery device according to claim 1, wherein the adapter comprises a threaded area for engaging a threaded needle hub of the injection needle.

13. The drug delivery device according to claim 1, wherein a spring is arranged for biasing the movable body component towards the aligned position or towards the misaligned position.

14. The drug delivery device according to claim 1, wherein the movable body component and the main component are arranged to form a slide restraint, wherein the slide restraint is arranged for limiting movement of the movable body component.

* * * * *